United States Patent [19]

Betts

[11] Patent Number: 5,683,682

[45] Date of Patent: Nov. 4, 1997

[54] DERIVATIVES OF AROMATIC BENZOATES AS INHIBITORS OF ESTERASE-PRODUCING MICRO-ORGANISMS

[75] Inventor: John Adrian Betts, Haslemere, United Kingdom

[73] Assignee: Robertet S.A., Grasse, France

[21] Appl. No.: 856,955

[22] PCT Filed: Nov. 13, 1990

[86] PCT No.: PCT/GB90/01750

§ 371 Date: Jun. 9, 1992

§ 102(e) Date: Jun. 9, 1992

[87] PCT Pub. No.: WO91/07165

PCT Pub. Date: May 30, 1991

[30] Foreign Application Priority Data

Nov. 15, 1989 [GB] United Kingdom ............... 8925833

[51] Int. Cl.[6] .............. A61K 7/32; A61K 31/235
[52] U.S. Cl. ................ 424/65; 512/1; 574/533
[58] Field of Search ................................. 424/65

[56] References Cited

FOREIGN PATENT DOCUMENTS

| | | | |
|---|---|---|---|
| 0011002 | 5/1980 | European Pat. Off. | 252/300 |
| 0213841 | 3/1987 | European Pat. Off. | 252/300 |
| 2108219 | 5/1972 | France . | |
| 60-199859 | 10/1985 | Japan | 424/DIG. 1 |
| 1293626 | 10/1972 | United Kingdom | 514/230 |
| 1388857 | 3/1975 | United Kingdom | 514/1 X |
| 1425390 | 2/1976 | United Kingdom | 424/59 |
| 1427390 | 3/1976 | United Kingdom | 252/300 X |
| 1519690 | 8/1978 | United Kingdom | 514/230 |
| 1583219 | 1/1981 | United Kingdom | 514/230 |
| 2182037 | 5/1987 | United Kingdom | 252/300 X |
| PCTJP8500021 | 8/1985 | WIPO | 514/330 |
| PCTGB8604327 | 7/1986 | WIPO | 252/300 X |
| PCTGB8700323 | 11/1987 | WIPO . | |

*Primary Examiner*—Shelley A. Dodson
*Attorney, Agent, or Firm*—James Creighton Wrya

[57] ABSTRACT

Inhibitors of esterase-producing micro-organisms comprise, as active ingredient, a benzyl or phenyl benzoyloxybenzoate (I) which is hydrolysed by esterases to produce three mono-nucler benzene compounds which between them bear at least two hydroxyl and two carboxyl substances, and which which an anti-microbial action. The inhibitors may be formulated as personal deodorants or dermatological agents.

4 Claims, 1 Drawing Sheet

DERIVATIVES OF AROMATIC BENZOATES AS INHIBITORS OF ESTERASE-PRODUCING MICRO-ORGANISMS

BACKGROUND OF THE INVENTION

This invention relates to derivatives of aromatic benzoates as inhibitors of esterase-producing micro-organisms, for use primarily in deodorant compositions.

The human skin has a large natural population of micro-organisms. These organisms are nourished by various skin-secreted substances, skin cell debris, breakdown products of the skin and the organisms themselves. The skin secretions are conveniently divided into two groups, those containing water-soluble materials and constituted by eccrine and apocrine sweat, and sebum which contains lipid-soluble materials. These secretions will be referred to as 'liquid body-secretions' and they will now be described, as will their functions as they are generally understood.

Eccrine sweat consists mainly of a watery solution of dissolved salts and is produced by glands distributed over the whole skin surface. In conditions of occlusion, e.g. feet enclosed in socks and shoes, the eccrine sweat accumulates, and in these warm damp conditions, the skin debris, together with nutrients from the sweat, provide a medium for micro-organism growth with the possibility of massive overgrowth of one type. This can result, in the first instance, in odorous metabolic products, and in the second, in clinical infection with maceration of the skin and irritation.

Apocrine sweat is produced by the apocrine glands at specific sites on the body, notably the axillae, the anogenital area and around the nipples. Although present at birth, the apocrine glands are not functional until puberty when they are influenced by circulating androgens. Apocrine secretion differs from eccrine sweat in containing lipids (fatty materials) and proteins. In the warm, damp occlusion met in the axillae, certain skin micro-organisms metabolise this secretion, forming free fatty acids and other breakdown products. These materials are odorous and responsible for 'body odour'.

The sebaceous glands are distributed over the skin surface except the palms and dorsae. They are most numerous on the scalp, forehead, face, back and chest. The secretion, sebum, consists mainly of fatty materials, wax esters, cholesterol and its esters and squalene. Normally, sebum flows freely from the glands, spreading over the skin surface. In acneic and certain other skin conditions, the sebaceous duct through which the sebum is normally secreted becomes hyperkeratinised and the opening of the duct becomes blocked. The gland continues to produce sebum and the blocked duct distends to form a comedone. Also blocked in the duct, the (normally) commensal micro-organisms produce esterases which hydrolyse the sebum lipids, liberating free fatty acids. These fatty acids are irritant and can result in an inflammatory reaction along the wall of the duct. Leucocytes invade the inflamed area and the comedone develops into a papule and then a pustule. This is a typical acne 'spot'.

The scalp is well supplied with sebaceous glands, and the scalp, like all skin, undergoes desquamation. Due to the presence of hair, the squames tend to be retained at the scalp surface. Sebum accumulates beneath these squames and in dandruff conditions is hydrolysed by micro-organism produced esterases to form irritant fatty acids. The irritation causes proliferation of the epidermis and increased formation of the stratum corneum which again desquamates unevenly in large clumps—the dandruff scale or flake.

In our International Application No. PCT/GB87/00323 (Publication No. WO87/06827) we disclosed an inhibitor of esterase-producing microorganisms in which the active ingredient comprised an aromatic acid ester of a phenol or of an aromatic alcohol, the phenol or aromatic alcohol being sufficiently water-soluble to impart an anti-microbial action and the aromatic acid being sufficiently water-soluble to impart an anti-microbial action and/or to lower the pH of liquid body-secretion to a level which at least inhibits the growth of micro-organisms in the liquid body-secretions; for use in deodorants the active ingredient may be incorporated in a perfume composition which is then incorporated in a vehicle such as ethanol; for use in a dermatological composition, the active ingredient may be incorporated in an acceptable vehicle containing for example, a polyol or dimethyl suphoxide which may also act as a skin penetrant.

The effect of the active ingredient is produced by the aforementioned microbial enzymes acting to split the constituents of the ester and so hydrolyse the ester back into the aromatic acid and the phenol or aromatic alcohol. On a skin surface, such as in deodorant applications, this action occurs almost immediately but, where skin penetration is involved, as in most dermatological applications, the action is progressive.

The above term 'anti-microbial action' means an action which inhibits microbial growth, rather than one which eliminates microbial growth completely as can be achieved by a microbicide. In such skin-surface and skin-penetrating applications, the esterases produced by the micro-organism hydrolyse a portion of the active ingredient and, in so doing, inhibit the action of the esterase and further growth of the micro-organism. After a period of time, the micro-organism may resume its metabolic activity and the above-mentioned process is repeated, and repetition will occur until the active ingredient is used up.

DESCRIPTION OF THE INVENTION

According to the present invention we have now found that phenyl or benzyl benzoates of the following general formula (I)

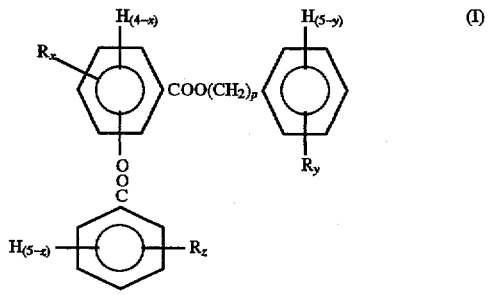

wherein R represents a hydrogen or halogen atom or a $C_{1-4}$ alkyl, methoxy, ethoxy or acyloxy group, p is 0 or 1, and x, y and z are each 0 or an integer of from 1 to 5, are particularly effective as inhibitors of esterase-producing micro-organisms.

Figure 1:
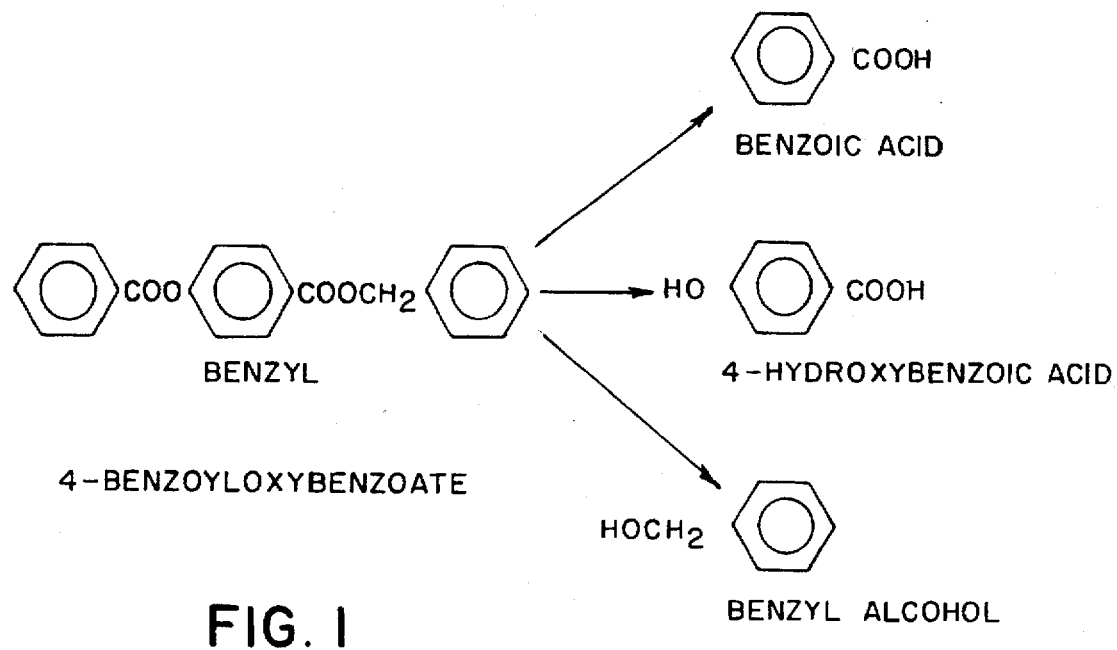
FIG. 1 shows the hydrolysis of benzyl 4-benzoyloxybenzoate.
Figure 2:
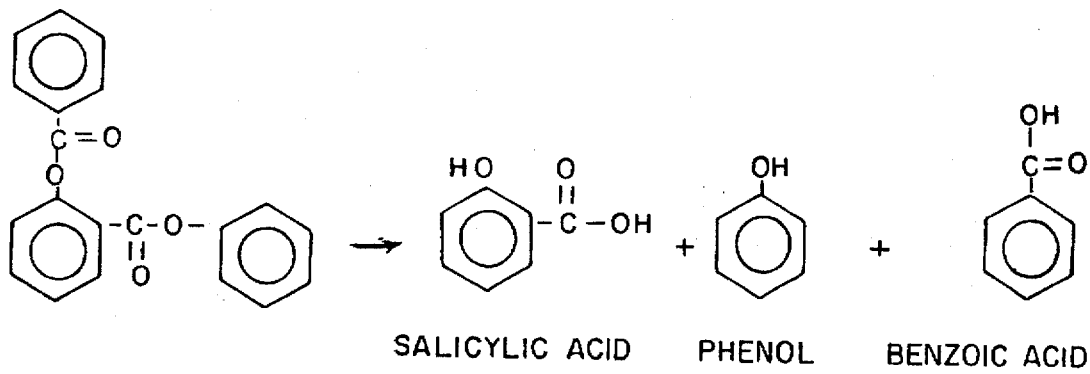
FIG. 2 shows the hydrolysis of phenyl 2-benzoyloxybenzoate.

Benzoates of the formula (I) are hydrolysed by esterases to produce three mononuclear benzene compounds which between them bear at least two hydroxyl substituents and two carboxyl substituents. (The hydrolysis of benzyl 4-benzoyloxybenzoate and phenyl 2-benzoyloxybenzoate are shown in FIGS. 1 and 2, respectively, of the accompanying drawings.) The hydrolysis products are thus highly active in performing the previously-mentioned antimicrobial and pH-lowering functions, but not to the extent of being bacteriocidal as are most conventional deodorants: not only is the elimination of cutaneous flora medically undesirable, but the use of some conventional deodorants has caused adverse reactions. Moreover, the benzoates (I) afford the further advantages of being completely odourless and non-irritant.

Preferred benzoates (I) are those in which p equals 0 or 1; and x, y and z are each zero. Such compounds have the advantage of being easy to manufacture from cheap starting materials, although the 4-benzoyloxybenzoates are preferred from the point of view of easy purification, being solids and therefore easy to crystallize. Such unsubstituted benzoates (I) have the further advantage of being generally more soluble than compounds having substituted nuclei.

Although the presence of hydroxyl substituents on the nuclei of the parent molecule increases its solubility in water, such hydroxyl substitution can lead to increased toxic effects, and is therefore generally less preferred: and although the presence of halogen substituents increases the activity of the hydrolysis products, such halogen substitution can again lead to increased toxic effects and is also less preferred. As the 2-benzoyloxybenzoates of the general formula (I) yield a salicylic acid among their hydrolysis products, which can have an irritant effect, and the presence of a group at the 2-position can give rise to instability because of steric hindrance, and as the 3-benzoyloxybenzoates are more expensive to produce, the 4-benzoyloxybenzoates are generally preferred.

The primary use of benzoates (I) is as the active ingredient in a personal deodorant composition. For such an application the benzoate is first dissolved in, preferably, a perfume to form a perfume concentrate containing 5% to 50%, preferably say 10% benzoate, which is then added in an amount of about 1% to 2% to a suitable vehicle, for example ethyl alcohol, to form a deodorant composition in which the active ingredient is present in an amount of 0.1% to 0.2% and which is suitable for application by aerosol or mechanical spray.

A further use of the benzoates (1) is in the treatment of dandruff and acne where decomposition of the skin fats causes irritation. To prepare a skin lotion, for the treatment of acne, between 0.5% and 20%, and preferably about 5%, of active ingredient is incorporated in a vehicle which may be composed of dimethyl sulphoxide, polyol, ethanol and water in suitable proportions. Anti-inflammatory substances such as hydrocortisone or glycyrrhetic acid and healing agents such as allantoin, may also be incorporated in the end product.

As a scalp lotion for the treatment of dandruff, active ingredient within the above percentages is incorporated in a hydro-alcoholic vehicle, using solubilising agents as necessary.

As a powder for the treatment of tinea pedis and foot odour, active ingredient (if liquid), within the above percentages, is adsorbed onto amorphous silica powder or light magnesium carbonate which is then mixed with say 50% talcum, starch or other suitable powder. If the active ingredient is solid, usually crystalline, the crystals are finely ground, for example in a microniser, and then mixed with say 50% talcum, starch or other suitable powder.

Suitable perfume compositions may also be incorporated in the scalp/skin lotions and foot powders.

The skin and scalp lotions may be supplied in sprinkler bottles for application to the scalp or the affected skin area in the form of liquid droplets which are massaged into the scalp/skin. Alternatively, the lotion may be applied by means of a pad or compress which is pre-impregnated and supplied in a sealed package; the pad is partially exposed and then applied to an affected skin area, at least once per day. In further alternative forms, the inhibitors for use in treating the scalp or skin may comprise ointments, gels, creams, lotions, sprays or powders.

The inhibitors for foot treatment are preferably in powder form, as indicated above, but might also be supplied as liquids or in sprays etc.

An example of the preparation of what is believed to be the most soluble and active ingredient for use in the above compositions will now be described.

EXAMPLE

Preparation of Benzyl-4-benzoyloxybenzoate 0.5 mol (114 g) of benzyl 4-hydroxybenzoate was dissolved in 500 mol of 5% sodium hydroxide solution. 0.51 mol (72 g) of benzoyl-chloride was then added with rapid stirring. The reaction began almost immediately accompanied by a rise in temperature.

The reaction was completed in about 30 minutes when the odour of benzoyl chloride had disappeared and benzyl 4-benzoyloxybenzoate had precipitated as a fine powder or dense oil. The reaction mixture was then cooled and the aqueous liquid decanted. The reaction product was washed with water until the washings were neutral, and then filtered. Finally the crude product was recrystallized from hot 80% ethanol.

The reaction scheme may be represented as follows:

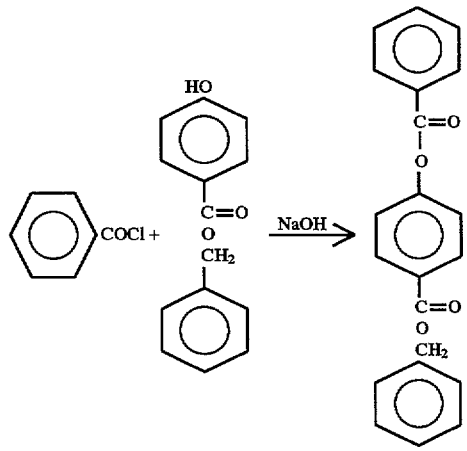

It will be appreciated that all the substituted products may be prepared by this general method.

I claim:

1. A deodorant composition comprising an aromatic benzoate having a general formula:

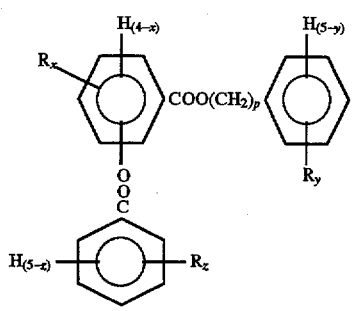 (I)

where R is a hydrogen or halogen atom or a $C_{1-4}$ alkyl, methoxy, ethoxy or acyloxy group, p is 0 or 1, and x, y and z are each 0 or an integer of from 1 to 5 and a vehicle.

2. The deodorant composition of claim 1, further comprising a perfume composition.

3. The deodorant composition of claim 1, wherein said aromatic benzoate of general formula (I) is a 4-benzoyloxybenzoate.

4. The deodorant composition of claim 2, wherein said aromatic benzoate of general formula (I) is a 4-benzoyloxybenzoate.

* * * * *